United States Patent
Aamir et al.

(10) Patent No.: US 11,866,349 B1
(45) Date of Patent: Jan. 9, 2024

(54) METHOD OF CHROMIUM ($CR^{+6}$) REMOVAL FROM WASTEWATER USING COPPER AUGMENTED BIOCHAR

(71) Applicant: King Faisal University, Al-Ahsa (SA)

(72) Inventors: Muhammad Aamir, Al-Ahsa (SA); Muhammad Hassan, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/242,418

(22) Filed: Sep. 5, 2023

(51) Int. Cl.
| | |
|---|---|
| C02F 1/28 | (2023.01) |
| B01J 20/02 | (2006.01) |
| B01J 20/20 | (2006.01) |
| B01J 20/30 | (2006.01) |
| B01J 20/32 | (2006.01) |
| C02F 1/62 | (2023.01) |
| A61K 36/899 | (2006.01) |
| C02F 101/22 | (2006.01) |
| B01J 20/28 | (2006.01) |
| C02F 1/68 | (2023.01) |

(52) U.S. Cl.
CPC .......... *C02F 1/283* (2013.01); *B01J 20/0237* (2013.01); *B01J 20/20* (2013.01); *B01J 20/3028* (2013.01); *B01J 20/3078* (2013.01); *B01J 20/3085* (2013.01); *B01J 20/3214* (2013.01); *B01J 20/3236* (2013.01); *C02F 1/62* (2013.01); *A61K 36/899* (2013.01); *B01J 20/28009* (2013.01); *C02F 1/683* (2013.01); *C02F 2101/22* (2013.01)

(58) Field of Classification Search
USPC ................ 210/660–693, 695, 702–749, 767, 210/911–913
See application file for complete search history.

(56) References Cited

U.S. PATENT DOCUMENTS

2020/0299157 A1* 9/2020 Kettunen ................ C02F 3/306

FOREIGN PATENT DOCUMENTS

| CN | 104437422 A | * | 3/2015 | ............. A41D 13/11 |
|---|---|---|---|---|
| CN | 106316683 A | * | 1/2017 | |
| CN | 106316683 A | | 1/2017 | |
| CN | 112871134 A | * | 6/2021 | ............. B01D 53/02 |
| CN | 115041165 A | * | 9/2022 | |
| CN | 115041165 A | | 9/2022 | |
| CN | 115634664 A | | 1/2023 | |

OTHER PUBLICATIONS

Wang et al. (Toxics, 2022, 10, 316). (Year: 2022).*
Hu et al. (Water Science & Technology, 2019, 80.12, 2260-2272). (Year: 2019).*
Chen et al. (Front. Chem. 11:1238424, published Aug. 30, 2023. (Year: 2023).*

(Continued)

*Primary Examiner* — Clare M Perrin
(74) *Attorney, Agent, or Firm* — Nath, Goldberg & Meyer; Richard C. Litman

(57) ABSTRACT

A method of chromium removal from wastewater comprising providing a copper augmented biochar and contacting the copper augmented biochar with the wastewater to remove chromium from the wastewater. The copper augmented biochar can remove chromium from wastewater with about 99% efficiency in about 1 hour.

7 Claims, 1 Drawing Sheet

Production of Biochar through pyrolysis

Pyrolysis Setup

(56) References Cited

OTHER PUBLICATIONS

Machine translation of CN 104437422 A, pp. 1-6. (Year: 2015).*
Machine translation of CN-112871134-A, pp. 1-12. (Year: 2021).*
Machine translation of CN 106316683 A, pp. 1-7. (Year: 2017).*
Machine translation of CN 115041165 A, pp. 1-8. (Year: 2022).*
NPL-1: Ambika et al., "Modified Biochar as a Green Adsorbent for Removal of Hexavalent Chromium From Various Environmental Matrices: Mechanisms, Methods, and Prospects", Chemical Engineering Journal, vol. 439, Jul. 1, 2022, 135716.
NPL-2: Zhao et al., "Microscopic Mechanism About the Selective Adsorption of CR(VI) From Salt Solution On O-Rich and N-Rich Biochars", Journal of Hazardous Materials, vol. 404, Part A, Feb. 15, 2021, 124162.

* cited by examiner

METHOD OF CHROMIUM (CR$^{+6}$) REMOVAL FROM WASTEWATER USING COPPER AUGMENTED BIOCHAR

BACKGROUND

1. Field

The present disclosure relates to methods of chromium removal from wastewater.

2. Description of the Related Art

Despite the popular knowledge that over two-thirds of the earth's surface area is covered by water, only about 2.5% of this water is available as freshwater, of which 69% is in the form of ice caps and glaciers. The need to recycle the limitedly available water is, therefore, inevitable.

Metals disposed in water from various human activities, specifically industrial activities, even at trace levels, are a potential threat to animals and ultimately humans as they are non-biodegradable and their bioaccumulation in the human body can cause various diseases and disorders. Chromium (Cr$^{+6}$) pollution, for example, is very dangerous for the environment, aquaculture, and ground water due to its potential carcinogenicity impacts when ingested.

Thus, new methods of chromium removal from wastewater solving the aforementioned problems are desired.

SUMMARY

In an embodiment, the present subject matter relates to a method of chromium removal from wastewater comprising providing a copper augmented biochar and contacting the copper augmented biochar with the wastewater to remove chromium from the wastewater. In some embodiments, the copper augmented biochar can remove chromium from wastewater with about 99% efficiency in about 1 hour.

Accordingly, in an embodiment, the present subject matter relates to a method of removing chromium from wastewater, the method comprising: providing a copper augmented biochar; contacting the copper augmented biochar with the wastewater; and
  removing the chromium from the wastewater using the copper augmented biochar.

In another embodiment, the present subject matter relates to a method of preparing copper augmented biochar comprising pyrolyzing wheat straw to provide a biochar and adding copper to the biochar to provide a copper augmented biochar. In an embodiment, the wheat straw can be pyrolyzed for a period of time ranging from about 1.5 hours to about 3 hours at a temperature ranging from about 400° C. to about 600° C.

Accordingly, in a further embodiment, the present subject matter relates to a method of preparing copper augmented biochar comprising: pyrolyzing wheat straw to provide a biochar; and adding copper to the biochar to provide a copper augmented biochar.

These and other features of the present subject matter will become readily apparent upon further review of the following specification.

DETAILED DESCRIPTION OF THE PREFERRED EMBODIMENTS

Figure 1:
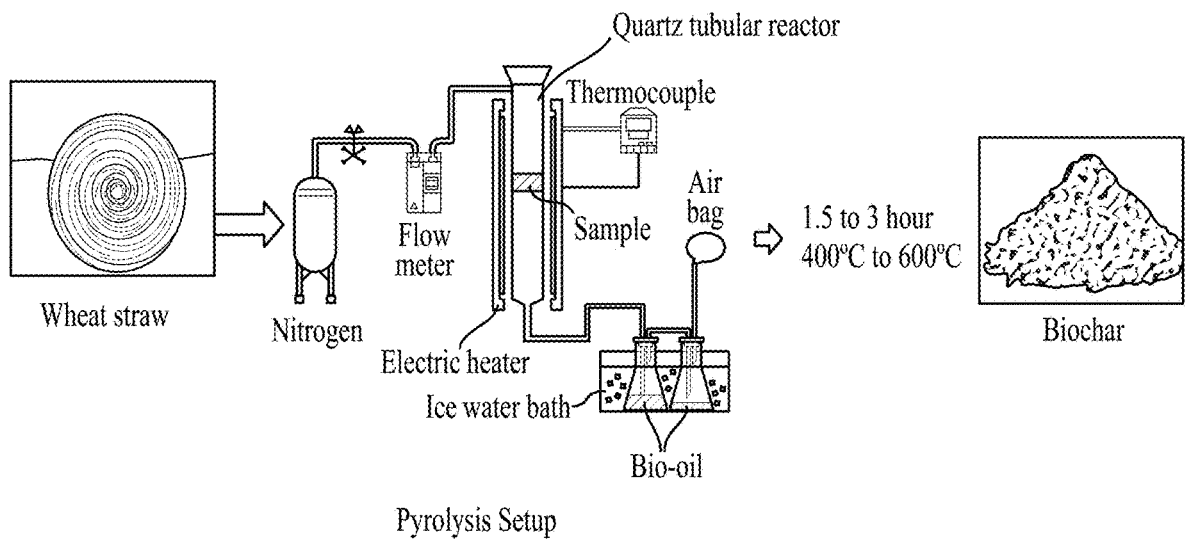
FIG. 1 is a schematic diagram illustrating the method for preparing biochar from wheat straw according to the present teachings.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a method of chromium removal from wastewater comprising providing a copper augmented biochar, contacting the copper augmented biochar with the wastewater, and removing chromium from the wastewater using the biochar. In some embodiments, the copper augmented biochar can remove chromium from the wastewater with about 99% efficiency in about 1 hour.

Figure 2:
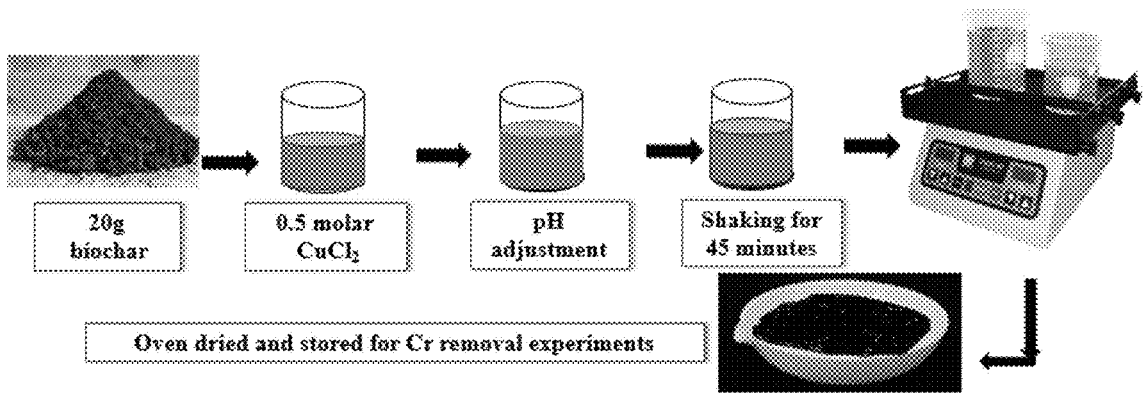
FIG. 2 is a schematic diagram illustrating the method for preparing a copper augmented biochar according to the present teachings.

In a further embodiment, the present subject matter relates to a method of removing chromium from wastewater, wherein the copper augmented biochar can be prepared by pyrolyzing wheat straw to provide a biochar; and adding copper to the biochar to provide a copper augmented biochar (FIGS. 1 and 2). Wheat straw, as used herein, refers to the byproduct or leftover remaining once wheat grain is harvested. In an embodiment, the wheat straw is dried and ground prior to pyrolyzing.

In a further embodiment, the wheat straw can be ground to particle sizes ranging from about 0.3 mm to about 1.0 mm. For example, the wheat straw can be ground to a particle size of about 0.5 mm.

In an additional embodiment, the wheat straw can be pyrolyzed for a period of time ranging from about 1.5 hours to about 3 hours at a temperature ranging from about 400° C. to about 600° C. In one embodiment, the wheat straw can be pyrolyzed for a period of time ranging from about 2 hours to about 2.5 hours at a temperature ranging from about 400° C. to about 600° C. In an embodiment, the wheat straw can be pyrolyzed at a temperature of about 550° C. In an embodiment, an inert atmosphere is provided in the pyrolyzer by passing nitrogen therethrough.

In another embodiment, the present subject matter relates to a method of chromium removal from wastewater, wherein the copper augmented biochar is prepared by combining the biochar formed from wheat straw with $CuSO_4$ and water to form a solution, mixing the solution while heating to provide a heated solution; obtaining wet biochar from the heated solution; and heating the wet biochar for a period of time ranging from about 1 hour to about 3 hours at a temperature ranging from about 550° C. to about 650° C. to provide a copper augmented biochar.

In an embodiment, the wet biochar is obtained by heating the heated solution in an oven. In an embodiment, the solution is mixed for a period of time ranging from about 40 minutes to about 60 minutes at a temperature ranging from about 45° C. to about 55° C. In an embodiment, the solution is mixed for about 45 minutes at about 50° C.

In an embodiment, about 5 grams to about 10 grams of biochar can be mixed with about 1 gram to about 3 grams of copper sulfate and about 30 grams to about 50 grams of water. In an embodiment the water is deionized. In an embodiment, about 8 grams of biochar can be mixed with about 2 grams of copper sulfate ($CuSO_4$) and about 40 grams of deionized water to form the heated solution.

In an embodiment, the wet biochar is heated in, by way of non-limiting example, a muffle furnace for a period of time ranging from about 1 hour to about 3 hours at a temperature ranging from about 550° C. to about 650° C. In an embodiment, the wet biochar can be heated in, by way of non-limiting example, a muffle furnace, for about 2 hours at 600° C.

In one embodiment, the copper augmented biochar can be contacted with the wastewater for a period of time ranging from about 0.5 hours to about 1.5 hours to remove chromium from the wastewater. In an embodiment, the chromium can be obtained from chromium(III) chloride hexahydrate in the wastewater. In an embodiment, a concentration of chromium (III) chloride hexahydrate in the wastewater can range from about 0.1 mg/L to about 0.5 mg/L. In an embodiment, a concentration of chromium(III) chloride hexahydrate can be about 0.2 mg/L.

In an embodiment, the present subject matter relates to a method of preparing a copper augmented biochar by pyrolyzing wheat straw to provide a biochar; and adding copper to the biochar to provide a copper augmented biochar. In an embodiment, the wheat straw is dried and ground prior to pyrolyzing.

In an embodiment, the Cu augmented biochar can remove chromium from wastewater with a removal efficiency of about 85% to about 99% within about 60 minutes reaction time. In an embodiment, chromium removal comprises removal of hexavalent chromium ($Cr^{+6}$) from the wastewater. In an embodiment, the copper augmented biochar can achieve about 85% $Cr^{+6}$ removal within about 20 minutes of initial contact with the wastewater. In another embodiment, the copper augmented biochar can achieve about 99% $Cr^{+6}$ removal within about 60 minutes of initial contact with the wastewater. The $Cr^{+6}$ removal efficiency can be increased with an increase in temperature. In an embodiment, the Cu augmented biochar can remove chromium from wastewater at temperatures ranging from about 18° C. to 40° C.

The present subject matter can be better understood by referring to the following examples.

EXAMPLES

Example 1

Wheat straw was first air dried, then oven dried in an oven at 105° C. The dried wheat straw was then ground in a hammer mill to particles sizes as high as 0.5 mm and sieved. The pyrolyzer was then operated to temperatures between 400° C. and 600° C. and 50 grams of wheat straw powder was fed into the pyrolyzer chamber. The pyrolyzer was operated for 2 hours to 2.5 hours for each batch experiment before feeding the next batch (50 g of wheat straw) into the pyrolyzer chamber. The biochar was collected from the cup holder of the pyrolyzer. Nitrogen was continuously flowing through the pyrolyzer during the preparation of biochar to provide an inert environment. For the loading of the biochar, 08 grams of biochar was provided in an emerald flask and 02 grams of copper sulfate ($CuSO_4$) was added to that. 40 grams of deionized water was then added into the flask to form a solution and the solution was stirred for 45 minutes at 50° C. Afterwards, the solution was heated in an oven until a wet biochar was achieved. Then, the wet biochar was placed in a muffle furnace at 600° C. for 2 hours at a heating rate of 2° C./sec. The formation of copper augmented biochar was confirmed through XRD and FTIR analysis before the copper augmented biochar was used for chromium removal experiments.

Example 2

For the chromium removal experiments, chromium (III) chloride hexahydrate was utilized, and different concentration solutions were prepared (0.1-0.5) mg/L. The best results were achieved at a concentration of 0.2 mg/L. The chromium removal was confirmed through a spectrophotometer. Biochar without copper loading demonstrated 78% chromium removal within 60 minutes reaction time while the copper augmented biochar demonstrated $Cr^{+6}$ removal efficiency of up to 99% within 60 minutes reaction time. During the experiment, chromium removal was faster at the start of the experiment and slowed down with the progression of time. This was confirmed from the color of the solution which turned from yellow to colorless. Almost 85% $Cr^{+6}$ removal was recorded during the initial 20 minutes. The $Cr^{+6}$ removal efficiency increased with increased in temperature and moved from 87% to 98% when the temperature of the solution increased from 18° C. to 40° C.

It is to be understood that the present methods are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of preparing copper augmented biochar comprising:
    pyrolyzing wheat straw to provide a biochar; and
    adding copper to the biochar to provide a copper augmented biochar, wherein adding the copper to the biochar comprises mixing $CuSO_4$ and water with the biochar while heating to form a heated solution; obtaining a wet biochar from the heated solution; and heating the wet biochar for a period of time ranging from about 1 hour to about 3 hours at a temperature ranging from about 550° C. to about 650° C. to provide the copper augmented biochar.

2. The method of claim 1, wherein the wheat straw is dried and ground prior to pyrolyzing.

3. The method of claim 2, wherein the wheat straw is ground to particle sizes ranging from about 0.3 mm to about 1.0 m-mm.

4. The method of claim 1, wherein the wheat straw is pyrolyzed for a period of time ranging from about 1.5 hours to about 3 hours at a temperature ranging from about 400° C. to about 600° C.

5. The method of claim 1, wherein the wheat straw is pyrolyzed for a period of time ranging from about 2 hours to about 2.5 hours at a temperature ranging from about 400° C. to about 600° C.

6. The method of claim 1, wherein the wet biochar is heated in a muffle furnace for about 2 hours at about 600° C.

7. The method of claim 1, wherein the pyrolyzing step occurs in a presence of nitrogen gas.

\* \* \* \* \*